United States Patent
Tumlinson et al.

(10) Patent No.: US 9,332,902 B2
(45) Date of Patent: May 10, 2016

(54) LINE-FIELD HOLOSCOPY

(71) Applicant: Carl Zeiss Meditec, Inc., Dublin, CA (US)

(72) Inventors: Alexandre R. Tumlinson, San Leandro, CA (US); Matthew J. Everett, Livermore, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 597 days.

(21) Appl. No.: 13/745,632

(22) Filed: Jan. 18, 2013

(65) Prior Publication Data
US 2014/0028974 A1 Jan. 30, 2014

Related U.S. Application Data

(60) Provisional application No. 61/589,172, filed on Jan. 20, 2012.

(51) Int. Cl.
*A61B 3/14* (2006.01)
*A61B 3/10* (2006.01)
(Continued)

(52) U.S. Cl.
CPC ............ *A61B 3/102* (2013.01); *G01B 9/02043* (2013.01); *G01B 9/02044* (2013.01); *G01B 9/02047* (2013.01); *G01B 9/02091* (2013.01)

(58) Field of Classification Search
CPC .......... A61B 3/103; A61B 3/14; A61B 3/113; A61B 3/1015; A61B 3/152; A61B 3/107
USPC ......... 351/206, 210, 246, 205, 208, 209, 212, 351/221, 200
See application file for complete search history.

(56) References Cited

U.S. PATENT DOCUMENTS 7,602,501 B2   10/2009 Ralston et al.
2010/0195048 A1*   8/2010 Hammer .............. A61B 3/1025
                                                      351/206

(Continued)

FOREIGN PATENT DOCUMENTS

DE          4309056 B4    5/2006
WO       2012/143113 A1  10/2012

OTHER PUBLICATIONS

Zuluaga et al., "Spatially Resolved Spectral Interferometry for Determination of Subsurface Structure", Optics Letters, vol. 24, No. 8, Apr. 15, 1999, pp. 519-521.

(Continued)

*Primary Examiner* — Dawayne A Pinkney
(74) *Attorney, Agent, or Firm* — Morrison & Foerster LLP

(57) ABSTRACT

A novel imaging method, line-field holoscopy is presented. A line of light is projected across an object to be investigated through an imaging system. The light scattered from the investigated object is combined with reference radiation. The combined light is projected onto a detector providing a confocal restriction in one dimension. Astigmatic optics in the return path transform the light asymmetrically such that at the detector, the line focus is imaged to the confocal restriction, while the orthogonal direction is defocused. Embodiments including a swept source with linear detection array, and spectrometer based systems utilizing a 2D detector array are described. The data may be reconstructed to a B-scan by two-dimensional Fourier transform or other reconstruction method with or without combination of more complex algorithms.

14 Claims, 6 Drawing Sheets

(51) Int. Cl.
 A61B 3/00 (2006.01)
 G01B 9/02 (2006.01)

(56) References Cited

U.S. PATENT DOCUMENTS

2011/0273608 A1* 11/2011 Tsukada ............... G02B 7/36
 348/345
2012/0232535 A1 9/2012 Li et al.

OTHER PUBLICATIONS

Hillmann et al., "Holoscopy—Holographic Optical Coherence Tomography", Proc. of SPIE-OSA Biomedical Optics, vol. 8091, 2011, pp. 80911H-1-80911H-7.
Blazkiewicz et al., "Signal-To-Noise Ratio Study of Full-Field Fourier-Domain Optical Coherence Tomography", Applied Optics, vol. 44, No. 36, Dec. 20, 2005, pp. 7722-7729.
Franke et al., "High Resolution Holoscopy", Proc. of SPIE, vol. 8213, 2012, pp. 821324-1-6.
Hillmann et al., "Holoscopy—Holographic Optical Coherence Tomography", Optics Letters, vol. 36, No. 13, Jul. 1, 2011, pp. 2390-2392.
Mico et al., "Basic Principles and Applications of Digital Holographic Microscopy", Microscopy: Science, Technology, Applications and Education, 2010, pp. 1411-1418.
Nakamura et al., "High-Speed Three-Dimensional Human Retinal Imaging by Line-Field Spectral Domain Optical Coherence Tomography", Optics Express, vol. 15, No. 12, Jun. 11, 2007, pp. 7103-7116.
Adie et al., "Computational Adaptive Optics for Broadband Optical Interferometric Tomography of Biological Tissue", PNAS, vol. 109, May 8, 2012, pp. 7175-7180.
Adie et al., "Interferometric Synthetic Aperture Microscopy", Biomedical Applications of Light Scattering: McGraw Hill, 2009, 43 pages.
Alexandrov et al., "Synthetic Aperture Fourier Holographic Optical Microscopy", Physical Review Letters, vol. 97, Oct. 18, 2006, pp. 168102-1-168102-4.
Bonin et al., "In Vivo Fourier-Domain Full-Field Oct of the Human Retina with 1.5 Million A-lines/s", Optics Letters, vol. 35, No. 20, Oct. 15, 2010, pp. 3432-3434.
Cuche et al., "Spatial Filtering for Zero-Order and Twin-Image Elimination in Digital Off-Axis Holography", Applied Optics, vol. 39, No. 23, Aug. 10, 2000, pp. 4070-4075.
Dändliker et al., "Reconstruction of the Three-Dimensional Refractive Index from Scattered Waves", Optics Communications, vol. 1, No. 7, Feb. 1970, pp. 323-328.
Davis et al., "Interferometric Synthetic Aperture Microscopy: Computed Imaging for Scanned Coherent Microscopy", Sensors, vol. 8, Jun. 11, 2008, pp. 3903-3931.
Davis et al., "Nonparaxial Vector-Field Modeling of Optical Coherence Tomography and Interferometric Synthetic Aperture Microscopy", Journal of the Optical Society of America A, vol. 24, No. 9, Sep. 2007, pp. 2527-2542.
Desjardins et al., "Speckle Reduction in OCT using Massively-Parallel Detection and Frequency-Domain Ranging", Optics Express, vol. 14, No. 11, May 29, 2006, pp. 4736-4745.
Devaney, A. J., "Reconstructive Tomography with Diffracting Wavefields", Inverse Problems, vol. 2, 1986, pp. 161-183.
Endo et al., "Profilometry with Line-Field Fourier-Domain Interferometry", Optics Express, vol. 13, No. 3, Feb. 7, 2005, pp. 695-701.
Fechtig et al., "Line Field Off Axis Swept Source OCT Utilizing Digital Refocusing", Proc. of SPIE, 2014, 6 pages.
Fercher et al., "Image Formation by Inversion of Scattered Field Data: Experiments and Computational Simulation", Applied Optics, vol. 18, No. 14, Jul. 15, 1979, pp. 2427-2439.
Fercher et al., "Measurement of Intraocular Distances by Backscattering Spectral Interferometry", Optics Communications, vol. 117, May 15, 1995, pp. 43-48.

Fercher, Adolf F., "Optical Coherence Tomography", Journal of Biomedical Optics, vol. 1, No. 2, Apr. 1996, pp. 157-173.
Franke et al., "Towards Microscopic Resolution in Holoscopy", Proc. of SPIE, vol. 8571, 2013, pp. 85711O-1-85711O-6.
Grajciar et al., "High Sensitivity Phase Mapping with Parallel Fourier Domain Optical Coherence Tomography at 512 000 A-scan/s", Optics Express, vol. 18, No. 21, Oct. 11, 2010, pp. 21841-21850.
Grajciar et al., "High-Resolution Phase Mapping with Parallel Fourier Domain Optical Coherence Microscopy for Dispersion Contrast Imaging", Photonics Letters of Poland, vol. 3, No. 4, Dec. 31, 2011, pp. 135-137.
Grajciar et al., "Parallel Fourier Domain Optical Coherence Tomography for in Vivo Measurement of the Human Eye", Optics Express, vol. 13, No. 4, Feb. 21, 2005, pp. 1131-1137.
Grajciar et al., "Parallel Fourier Domain Optical Coherence Tomography, Measurement of the Human Eye in Vivo", Proc. of SPIE, vol. 5690, 2005, pp. 163-167.
Hillmann et al- "Common Approach for Compensation of Axial Motion Artifacts in Swept-Source OCT and spersion-D OCT", Optics Express, vol. 20, No. 6, Mar. 12, 2012, pp. 6761-6776.
Hillmann et al., "Efficient Holoscopy Image Reconstruction", Optics Express, vol. 20, No. 19, Sep. 10, 2012, pp. 21247-21263.
Kim, M. K., "Tomographic Three-Dimensional Imaging of a Biological Specimen Using Wavelength-Scanning Digital Interference Holography", Optics Express, vol. 7, No. 9, Oct. 23, 2000, pp. 305-310.
Kim, M. K., "Wavelength-Scanning Digital Interference Holography for Optical Section Imaging", Optics Letters, vol. 24, No. 23, Dec. 1, 1999, pp. 1693-1695.
Kim, Myung K., "Principles and Techniques of Digital Holographic Microscopy", SPIE Reviews, vol. 1, 2010, pp. 018005-1-018005-50.
Lee et al., "Line-Field Optical Coherence Tomography Using Frequency-Sweeping Source", IEEE Journal of Selected Topics in Quantum Electronics, vol. 14, No. 1, Jan./Feb. 2008, pp. 50-55.
Leith et al., "Wavefront Reconstruction with Diffused Illumination and Three-Dimensional Objects", Journal of the Optical Society of America, vol. 54, No. 11, Nov. 1964, pp. 1295-1301.
Marks et al., "Inverse Scattering for Frequency-Scanned Full-Field Optical Coherence Tomography", Journal of the Optical Society of America A, vol. 24, No. 4, Apr. 2007, pp. 1034-1041.
Massig, Jurgen H., "Digital Off-Axis Holography with a Synthetic Aperture", Optics Letters, vol. 27, No. 24, Optical Society of America, US, Dec. 15, 2002, pp. 2179-2181.
Mujat et al., "Swept-Source Parallel OCT", Proc. of SPIE, vol. 7168, 2009, pp. 71681E-1-71681E-8.
Nakamura et al., "Complex Numerical Processing for In-Focus Line-Field Spectral-Domain Optical Coherence Tomography", Japanese Journal of Applied Physics, vol. 46, No. 4A, 2007, pp. 1774-1778.
Nakamura et al., "Optimization of Line-Field Spectral Domain Optical Coherence Tomography for in Vivo High-Speed 3d Retinal Imaging", Proc. of SPIE, vol. 6429, 2007, pp. 64291P-1-64291P-6.
Pan et al., "A Computational Study of Reconstruction Algorithms for Diffraction Tomography: Interpolation Versus Filtered Backpropagation", IEEE Transactions on Acoustics, Speech, and Signal Processing, vol. ASSP-31, No. 5, Oct. 1983, pp. 1262-1275.
Potcoava et al., "Optical Tomography for Biomedical Applications by Digital Interference Holography", Measurement Science and Technology, vol. 19, May 23, 2008, pp. 1-8.
Ralston et al., "Interferometric Synthetic Aperture Microscopy", Nature Physics, vol. 3, Feb. 2007, pp. 129-134.
Ralston et al., "Real-Time Interferometric Synthetic Aperture Microscopy", Optics Express, vol. 16, No. 4, Feb. 18, 2008, pp. 2555-2569.
Ralston et al., "Inverse Scattering for Optical Coherence Tomography", Journal of the Optical Society of America A, vol. 23, No. 5, May 2006, pp. 1027-1037.
Rinehart et al., "Quantitative Phase Microscopy with Off-Axis Optical Coherence Tomography", Optics Letters, vol. 39, No. 7, Apr. 1, 2014, 1996-1999.

(56) References Cited

OTHER PUBLICATIONS

Slaney et al., "Diffraction Tomography", available at <http://proceedings.spiedigitallibrary.org/>, retrieved on Sep. 16, 2013, pp. 2-17.

Soumekh et al., "Fourier Domain Reconstruction Methods with Application to Diffraction Tomography", Acoustical Imaging, 1984, pp. 17-30.

Soumekh et al., "Image Reconstruction from Frequency Domain Data on Arbitrary Contours", IEEE International Conference on ICASSP '84, 1984, pp. 12A.2.1-12A.2.4.

Witte et al., "Short-Coherence Off-Axis Holographic Phase Microscopy Of Live Cell Dynamics", Biomedical Optics Express, vol. 3, No. 9, Aug. 22, 2012, pp. 2184-2189.

Wolf, Emil, "Three-Dimensional Structure Determination of Semi-Transparent Objects from Holographic Data", Optics Communications, vol. 1, No. 4, Sep./Oct. 1969, pp. 153-156.

Yasuno et al., "One-Shot-Phase-Shifting Fourier Domain Optical Coherence Tomography by Reference Wavefront Tilting", Optics Express, vol. 12, No. 25, Dec. 13, 2004, pp. 6184-6191.

Yasuno et al., "Non-Iterative Numerical Method for Laterally Super-resolving Fourier Domain Optical Coherence Tomography", Optics Express, vol. 14, No. 3, Feb. 6, 2006, pp. 1006-1020.

Yasuno et al., "Three-Dimensional Line-Field Fourier Domain Optical Coherence Tomography for In Vivo Dermatological Investigation", Journal Biomedical Optics, vol. 11, No. 1, Jan./Feb. 2006, pp. 014014-1-014014-7.

Yu et al., "Wavelength-Scanning Digital Interference Holography for Tomographic Three-Dimensional Imaging by Use of the Angular Spectrum Method", Optics Letters, vol. 30, No. 16, Aug. 15, 2005, pp. 2092-2094.

Yu et al., "Variable Tomographic Scanning with Wavelength Scanning Digital Interference Holography", Optics Communications, vol. 260, 2006, pp. 462-468.

Zhang et al., "Elimination of Zero-Order Diffraction in Digital Off-Axis Holography", Optics Communications, vol. 240, 2004, pp. 261-267.

Zhang et al., "Adaptive Optics Parallel Spectral Domain Optical Coherence Tomography for Imaging the Living Retina", Optics Express, vol. 13, No. 12, Jun. 13, 2005, pp. 4792-4811.

* cited by examiner

LINE-FIELD HOLOSCOPY

PRIORITY

This application claims priority to U.S. Provisional Application Ser. No. 61/589,172 filed Jan. 20, 2012 hereby incorporated by reference in its entirety.

TECHNICAL FIELD

The invention relates to the field of interferometric optical imaging. The invention provides a device that combines holoscopic acquisition and reconstruction techniques with a one dimensional confocal gate.

BACKGROUND

Hillmann et al have described holoscopy, which is similar to digital holography, where a full field Fourier Domain optical coherence tomography (FD-OCT) image is recorded by exposing a 2D sensor array to the light scattered from an object and reference surface from a swept frequency source (D. Hillmann et al, "Holoscopy—holographic optical coherence tomography" *Optics Letters* 36(13): 2390 2011 hereby incorporated by reference). In holoscopy, unlike classic OCT, the sensor array is typically imaged to the far field of the object rather than to the object. As a result, each sensor element on the 2D array records light scattered in a different direction, encoding a lateral spatial frequency, rather than light from a different position on the object. The axial spatial frequencies are encoded by the optical frequency of the source, just like in swept-source OCT. The data may be reconstructed to a volume by three-dimensional Fourier transform. The reconstruction is notable in that high lateral resolution and power efficiency can be achieved far from the equivalent Rayleigh range calculated from the numerical aperture of the system. Full field systems may also allow a greater amount of light (Maximum Permissible Exposure) than point scanning systems on sensitive tissues such as the eye as the illumination is not focused to a point on the retina. By detecting at a defocused plane, the reconstruction combines information from a larger number of sensor elements to a single output pixel. This method requires a very fast camera and a high power swept source. Full field systems are also particularly susceptible to multiply scattered photons, and light scattered or reflected from surfaces far from the object of interest because they have no confocal light restriction.

Nakamura et al described a line-field spectral domain OCT system that could acquire spectral domain data for a full B-scan in a single exposure of a 2D array (Y. Nakamura, et al, "High-speed three dimensional human retinal imaging by line-field spectral domain optical coherence tomography" *Optics Express* 15(12):7103 2007 hereby incorporated by reference). A vertical line of light was imaged onto the retina of an eye and reimaged onto the entrance silt of a spectrometer. Each point at the entrance slit of the spectrometer corresponded to a portion of the retina object under observation. The spectrometer decomposed the light from each point on the entrance slit of the spectrometer into a spectrum represented as a column on the 2D sensor. A standard SLD and common 2D image sensor could be used; effectively achieving a motion artifact free B-scan without very high speed electronics Like full field systems, the laterally distributed light allows a much greater exposure on sensitive tissues. Unlike the full field holoscopy systems described earlier, the sensor array in this design is imaged to the retina, rather than to the far field of the retina. The simple one-dimensional data reconstruction along the axial direction suggests that the system has the same limits of lateral resolution typically experienced by flying-spot OCT systems. The confocal gate in one lateral dimension, created by the narrow line illumination and the spectrometer entrance slit, is partially effective at eliminating light scattered from out of focus planes. Because of system aberrations, likely in the spectrometer, the system suffered from a strong SNR roll-off at the edges of the line profile.

SUMMARY

The subject invention is a special form of holoscopy that contains the advantages of both of the above techniques but avoids the disadvantages of each. A line of light is focused on an object to be investigated through an imaging system. The light scattered from the investigated object is combined with reference radiation and collected by a sensor array. An aspect of the invention is the introduction of astigmatic optics into the return path such that the narrow axis of the line focus is substantially imaged directly to the narrow axis of the detector and such that the line focus is defocused along its long axis on the sensor array. This results in a line of light at the sensor plane corresponding to the line of light on the retina, but where the lateral spatial frequency, or angular distribution of scattered light, is encoded along the line of detection. In a preferred embodiment, this line of light at the detection plane is projected onto the entrance slit of a spectrometer, such that at the 2D array sensor of the spectrometer, the spectral information along one axis of the sensor caries the axial frequency spectrum of the object, while the orthogonal direction encodes the lateral frequency information. The data may be reconstructed to a B-scan by two-dimensional Fourier transform with or without combination of more complex algorithms. In another embodiment, this line of light is projected onto a 1D sensor array and the illumination optical frequency is swept over time, resulting in the spectral information being encoded as a function of time, as in a swept source OCT system. A useful swept source produces a very narrow instantaneous bandwidth, which shifts with time such that a wide bandwidth is covered in short period of time, and sequential recordings at a detector, over the same time period, each contain a measurement of a very narrow optical frequency band.

The proposed solution, holoscopic line-field OCT, combines holoscopic acquisition and reconstruction techniques with a one dimensional confocal gate. It thus achieves a happy medium between the 'wide open' situation in full field holoscopy, which collects scatter even from surfaces very far from the object of interest; and the precisely confocal situation in point scanning flying-spot OCT systems. Allowing light to be detected at significant distances away from the focused region allows the system to better take advantage of digital refocusing techniques made possible by holoscopic reconstruction, without introducing the difficulties introduced by overwhelming reflections from surfaces such as the cornea of the eye. The image generation by the processor can involve reconstructing the output from the detector to transfer between optical frequency and angular direction to the spatial distribution of scattering in the object, wherein the optical frequency encodes the axial spatial frequency and the angular direction encodes the lateral spatial frequency. The reconstruction can include a digital wavefront propagation on the output from the detector to create a spatial distribution of scattering in the object. A preferred embodiment will possess the reconstruction advantages demonstrated by Hillmann with the economy of the Nakamura approach: high lateral resolution and power efficiency at a greater range of depths, with a simple SLD source and low speed 2D sensor array. Note that the amount of power allowed to be simultaneously incident across a line or area of the retina is far greater than the amount allowed focused to a point, allowing for far greater potential sensitivity than can be achieved by flying-spot OCT systems, particularly for objects where light exposure is limited such as the retina of the eye. Additionally the arrangement may have a SNR advantage due to the Fourier processing method as proposed by Blazkiewicz et al.

It should be noted that although the description above places the sensor plane at the far field of the retinal plane, one could also consider an intermediate case, where the astigmatic optics defocus the light along the long axis of the line focus, such that the interference for a single point on the retinal surface will be detected by multiple sensor elements, without defocusing all the way into the far field. In general, one would like to defocus the sensor by at least one Rayleigh length. In determining Rayleigh length we are concerned with the light as it hits the sensor and with dimension of concern in the long axis of the line focus. The light as emitted from a point in the scattering object, and transmitted through the limiting apertures of the optical system should be considered. In this case one maintains advantages conferred by detecting information from a single lateral location within the object plane upon a plurality of sensor pixels. Computational wavefront propagation from a generically defocused plane to a focused plane requires more complexity than the simple Fourier transform described in our preferred embodiment, however a plurality of methods for this task are well understood in the field of digital holography.

BRIEF DESCRIPTION OF THE FIGURES

FIGS. 2a, 2b and 2c illustrate one embodiment of the present invention wherein FIG. 2a illustrates the xz plane while FIG. 2b illustrates the yz plane. FIG. 2c again illustrates the yz plane, illustrating two additional beam paths.

FIGS. 3a and 3b illustrate an alternative and preferred embodiment of the present invention wherein FIG. 3a illustrates the xz plane while FIG. 3b illustrates the yz plane.

FIGS. 4a and 4b illustrate an embodiment of the invention using a swept-source and linear sensor array wherein FIG. 4a illustrates the xz plane while FIG. 4b illustrates the yz plane.

FIGS. 5a and 5b illustrate the data orientation on the sensor wherein FIG. 5a illustrates the 2D sensor inside the spectrometer of FIGS. 2a to 2c while FIG. 5b illustrates the 1D sensor of the embodiment described in FIGS. 4a and 4b at different times.

DETAILED DESCRIPTION

Figures 1A, 1B:
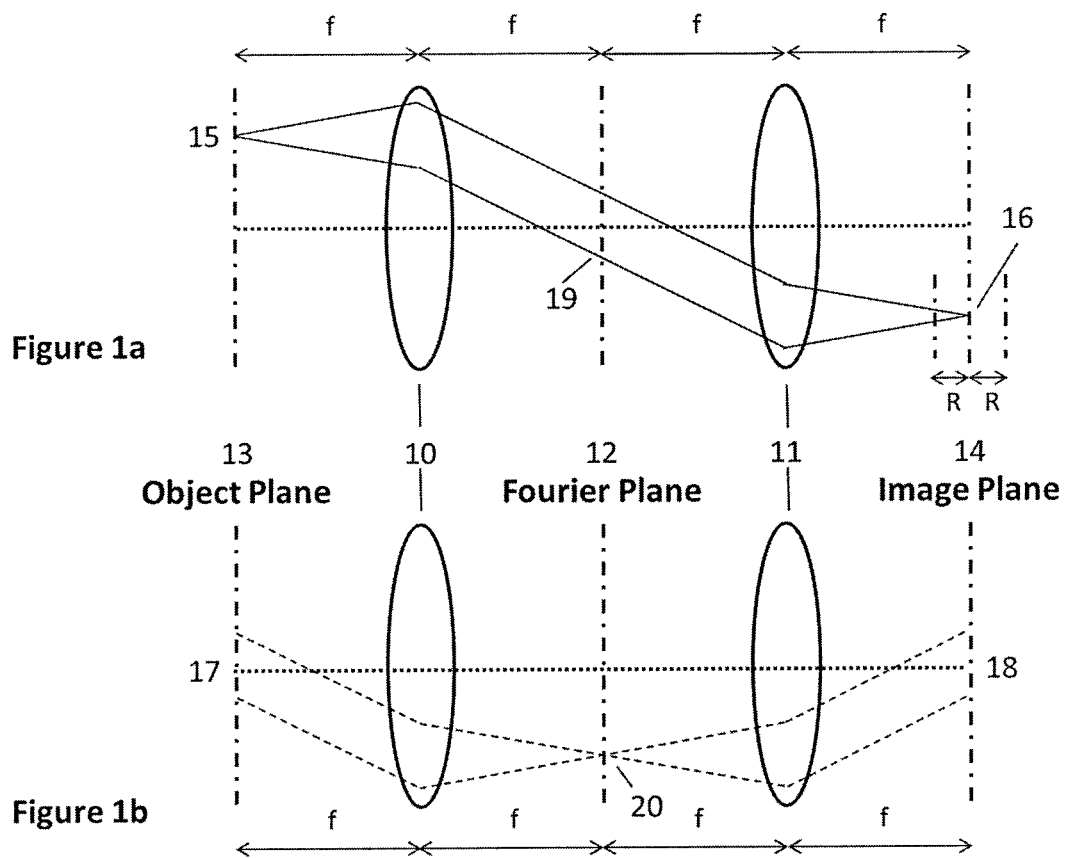
FIGS. 1a and 1b illustrate background concepts of conjugate planes and Fourier planes useful for understanding aspects of the present invention.

In the simplified optics described below, spaces are described with their imaging relationship to the object plane, which contains the object being investigated. Spaces within the system are identified as either optically conjugate to the object plane or at a Fourier plane with respect to the object plane. FIG. 1 is provided to illustrate these background concepts with a classic "4F" system. In the 4F system, a telescope is created with two lenses 10 and 11 each of focal length 'f'. A first, 'object', plane 13 is located one focal length in front of the first lens 10. An intermediate, 'Fourier', plane 12 is located at one focal length behind the first lens. The second lens 11 of focal length 'f' is placed a focal distance behind the intermediate plane. A third, 'image' plane 14 is located at one focal length behind the second lens. The first and the third planes 13 and 14 are 'optically conjugate'; there is a point to point correspondence of light in one plane to another as when traditionally imaged, as illustrated in FIG. 1a for points 15 and 16. Similarly, at optically conjugate planes there is a beam direction, to beam direction correspondence of light in one plane to another, as indicated in FIG. 1b for beams 17 and 18. At the intermediate 'Fourier' plane 12, light from a point in the object 15 corresponds to a collimated beam 19, or plane wave, and the angular orientation of the plane wave is determined by the position of the point in the object plane 13, as shown in FIG. 1a. Light from a collimated beam 17, or plane wave, in the object 13, corresponds to a point 20 in the Fourier plane 12; and the angular orientation of the plane wave in the object 13 is described by the position of the point in the Fourier plane 12, as shown in FIG. 1b.

The combination of plane waves at different incident angles results in sinusoidal interference which is well described by the spatial frequency of interference. We therefore describe different locations within a Fourier plane as containing the information about different spatial frequencies of the object plane. Pupil plane and 'far field' are used synonymously with a plane that is located at a Fourier plane relative to the object plane. Planes located between the object and Fourier plane, or between the Fourier and image plane can be described as defocused, but not entirely into the far field. The Rayleigh length denoted R in FIG. 1a, as used here, describes the distance from an image plane where the blur dimension increases by a factor of 2. Note that although the diagram illustrates point like imaging, real optical systems, have a limited spot dimension at an image plane. The full aperture of the optical system supports the transfer of plane waves from many directions. The sum of these plane waves can describe an arbitrary distribution of light. Further description of this formalism can be found in the book Linear Systems, Fourier Transforms, and Optics by Jack Gaskill hereby incorporated by reference.

In real cases it may be practical to design a system without strict maintenance of conjugate and Fourier planes at all interfaces, however it greatly simplifies the discussion of the important concepts to use these extremes. We therefore illustrate lenses such that, with an object plane at one focal distance away from the lens on a first side, the Fourier plane is located at one focal distance away from the lens on a second side. Because of astigmatic, asymmetrical elements such as cylindrical lenses, it is possible that a plane can be conjugate in one dimension, while it is a Fourier plane in the other dimension.

A key aspect of the invention is the introduction of astigmatic optics into the system such that the narrow axis of the line focus is substantially imaged directly to the narrow axis of the detector and such that the line focus is defocused along its long axis on the sensor array. This results in a line of light at the sensor plane corresponding to the line focus on the object, but where the lateral spatial frequency, or angular distribution of scattered light, is encoded along the line of detection. In general, one would like to defocus the sensor by at least one Rayleigh length. In determining Rayleigh length we are concerned with the light as it hits the sensor and with dimension of concern in the long axis of the line focus. The light as emitted from a point in the scattering object, and transmitted through the limiting apertures of the optical system should be considered. In this case one maintains advantages conferred by detecting information from a single lateral location within the object plane upon a plurality of sensor pixels. Computational wavefront propagation from a generically defocused plane to a focused plane requires more complexity than the simple Fourier transform described in our preferred embodiment, however a plurality of methods for this task are well understood in the field of digital holography (see for example Schnars et al. Digital Holography: Digital Hologram Reporting, Numerical Reconstruction, and Related Techniques Springer 2005).

Figure 2A:
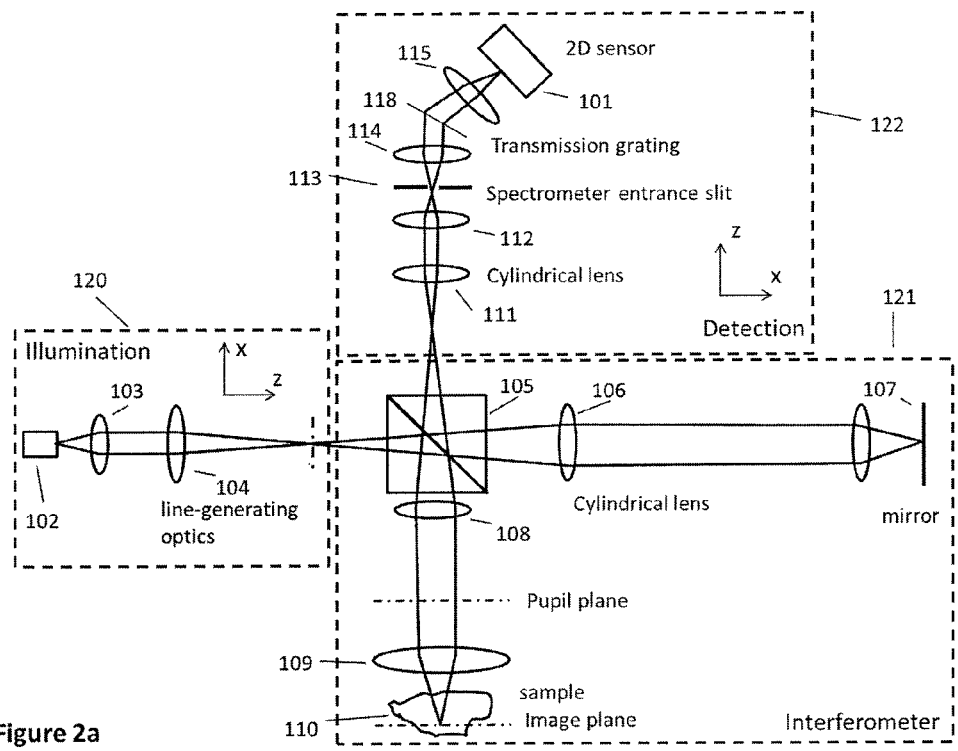
Figure 2B:
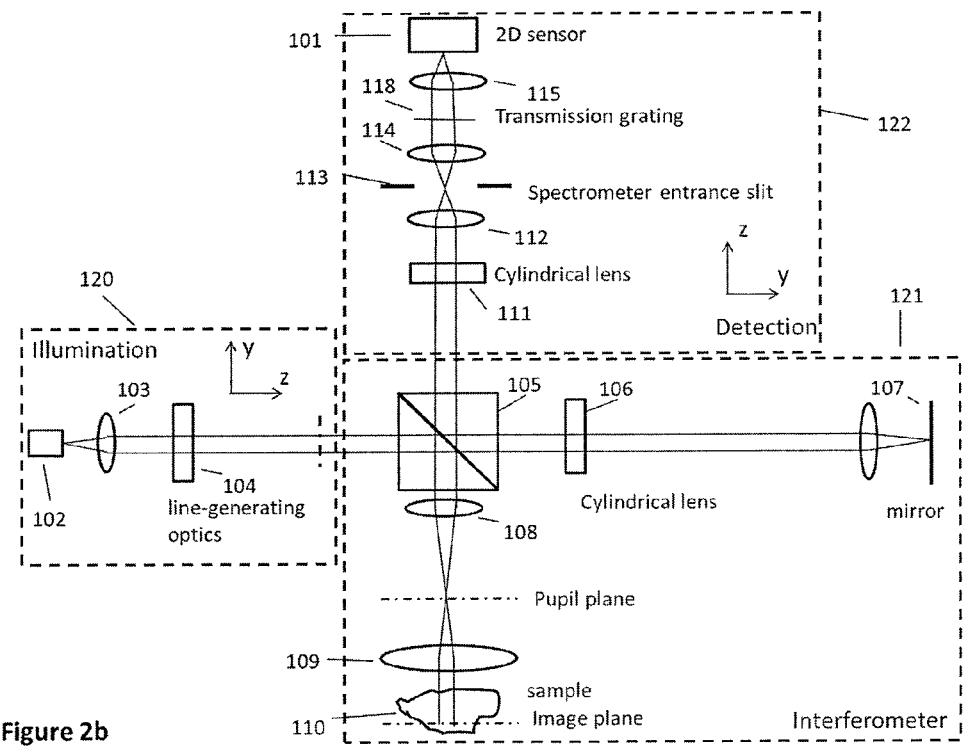
Figure 2C:
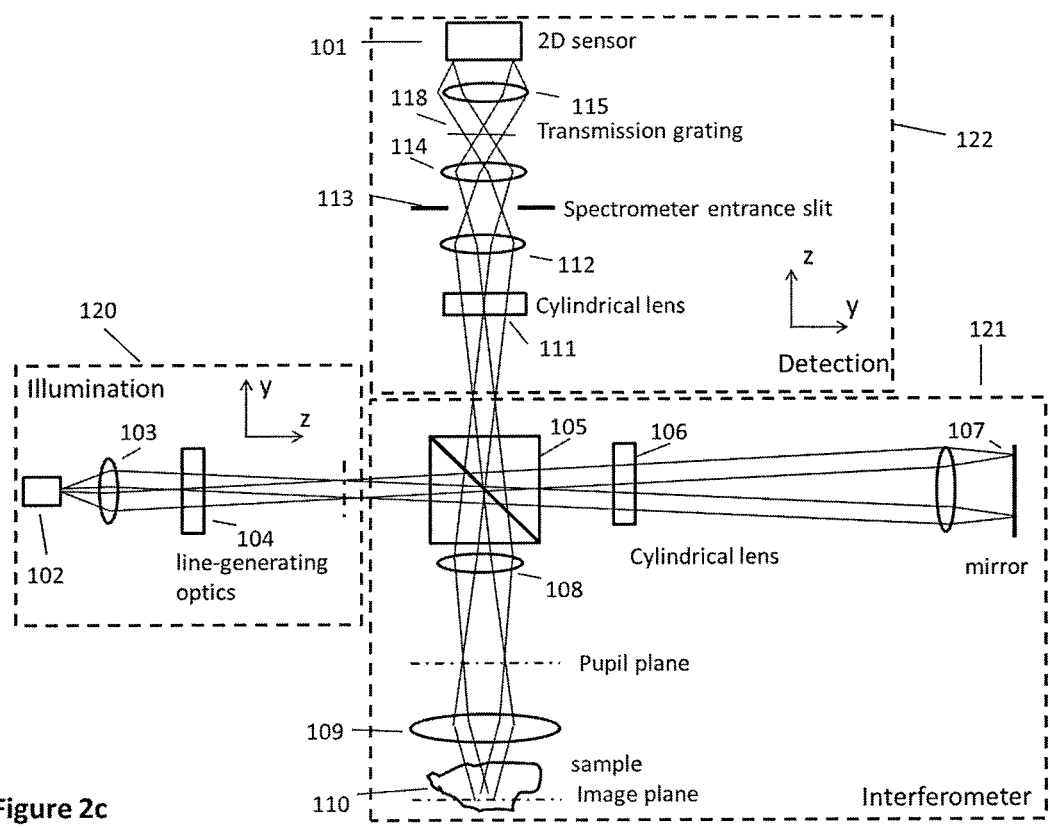

FIG. 2 illustrates a possible optical layout for a holoscopic line-field optical coherence tomography (OCT) system according to the present invention. The diagram is broken into three sections or blocks, illumination 120, interferometer 121, and detection 122. In this embodiment of the invention, the detection block includes collection optics and a spectrometer having an entrance slit 113, a dispersion element 118, and a two-dimensional sensor array 101. The figure is broken into two views. FIG. 2a shows a view with the x direction in the plane of the page. The beam path shown indicates the profile of the beam in the indicated axis. Where the profile narrows to a point, the beam is at an image plane relative to the sample plane in the indicated axis. In order to illustrate the layout of the orthogonal direction, FIG. 2b shows a view where the illumination and the spectrometer have been rotated by 90 degrees compared to FIG. 2a, i.e. with the y direction in the plane of the page. This view enables the visualization of the light path in the interferometer in the orthogonal direction as well. The beam path shown indicates the profile of a beam from a single direction, corresponding to the optical axis. Where the profile narrows to a point, the beam is at a Fourier plane relative to the sample plane in the indicated axis. FIG. 2c. shows the same orientation as FIG. 2b, however the beam paths shown indicate the profiles of beams from two extreme directions. Note that all illumination directions between these two extremes are present, including the beam represented in FIG. 2b. In the embodiment illustrated in FIG. 2, the astigmatic optical element is an astigmatic telescope introduced between the return path line focus created by the interferometer block and the spectrometer entrance slit. The astigmatic telescope is designed such that the long dimension of the line focus is defocused on the sensor array and the narrow dimension of the line focus is substantially imaged to the narrow axis of the entrance. The embodiment will now be described in further detail in reference to the figure.

Broadband light 102 passes through a collimating lens 103 and through optics 104 to generate a line shaped focus in a beam. A superluminescent diode (SLD) would be a typical light source, but any broadband light source could be used in the present invention and the line shape could be a property of the source instead of requiring additional optical elements. The source could also be swept in optical frequency as will be described further below. The line of light has extent in the y or vertical direction for this embodiment. The line of light is split into two paths of an interferometer at beam splitter 105. The light in one path, the reference arm, passes through a cylindrical lens 106 before reflecting off a minor 107. The purpose of the cylindrical lens is to substantially collimate the beam in both the x and y directions to make the arm relatively insensitive to changes in length, such that the arm may be modified to introduce a variable optical delay. Light in the second path, the sample arm of the interferometer, passes through spherical lens 108, which collimates the light in the x-dimension and focuses the line of light in the y-dimension to have a beam waist at the pupil plane. After passing the pupil plane, the light in the sample arm is focused to a line on the sample using one or more lenses 109. In the case of imaging the eye, focusing could be achieved all or in part using optical properties of the anterior segment of the eye itself. Light reflected from the sample and light reflected from the reference minor is recombined at beamsplitter 105 and directed towards the spectrometer entrance slit 113. The entrance slit is elongated in the y dimension as illustrated in FIGS. 2a and b. The dispersive element within the spectrometer, in this case a transmission grating 118, disperses the light in the x-dimension, perpendicular to the elongated axis. A cylindrical lens 111 and a spherical lens 112 prior to the entrance slit of the spectrometer form an astigmatic telescope that directly images the line focus in the x direction and defocuses the line focus on the sensor in the y direction, thus converting the positional content of the line in the y dimension into spatial frequencies of the y dimension. The narrow axis of the spectrometer entrance slit 113 is imaged back into the space of the scattering object and is substantially overlapping with the line focus of the illumination, acting as a confocal gate or confocal selecting mechanism in one dimension. The spectrometer contains a two-dimensional sensor array 101 for measuring the combined light from the signal and reference light paths. A processor is operably connected to the spectrometer for processing and reconstructing the data for image generation as will be described below. The processor can be part of the imaging device or be a stand-alone processor connected via cable or over the internet to the imaging device.

In fundamental contrast to the arrangement by Nakamura et al., positions across the x-direction on the 2D sensor correspond to optical frequencies and positions across the 2D sensor in the y-direction correspond to positions in the imaging pupil which in turn correspond to spatial frequencies in the line image (in the y-direction); rather than spatial positions along the line image. This is achieved by the insertion of astigmatic optics in the return path of the light towards the sensor.

Nakamura et al used an optical chopper to illuminate the detector with pulses of light in order to reduce the effect of phase washout that may occur if the object moves during the exposure time of the sensor. (Y. Nakamura, et al, "High-speed three dimensional human retinal imaging by line field spectral domain optical coherence tomography" *Optics Express* 15(12):7103 2007). A lower cost way to achieve this effect is to use an electronic shutter feature as provided by even many low cost 2D arrays. Global shuttering may provide a snapshot with the least sensitivity to motion, while rolling shutting may provide specific sensitivity to different types of motion. For example if a rolling shutter is introduced such that a range of optical frequencies across all lateral angles is exposed in sequence, axial motion will be encoded as a dispersion in the optical frequency information. An exposure efficient way to limit light without the complexity of mechanical chopping could include a pulsed electrical drive system to the illumination source.

After the interferometric data is collected, reconstruction of the data in the spatial frequency domain may be performed in the processor by "multiplication with a conjugated reference wave and propagation of the light waves by the angular spectrum approach" as described by Hillmann before or after reconstruction of the data in the spectral frequency domain. (D. Hillmann et al, "Holoscopy—holographic optical coherence tomography" *Optics Letters* 36(13): 2390 2011 hereby incorporated by reference). Ralston et al. propose alternative reconstruction techniques in U.S. Pat. No. 7,602,501. Propagation and reconstruction techniques to create a spatial distribution of scattering in the object are well understood in the field of Digital Holography and could be easily extended to the system described herein by someone skilled in the art. Because the data is in the spatial frequency domain in only in the y and z axes, and is already in the spatial domain in the x axis, methods are modified accordingly. That is, the conjugated reference wave has variations only in the y direction, and propagation should be performed in a 2 dimensional rather than 3 dimensional space, approximating that the beam phase is constant across the x dimension. A remapping function could be applied to shape the optical frequency spectrum and angular direction to a well behaved grid of spatial frequencies prior to two-dimensional Fourier transform. After reconstruction, various images can be generated of the data.

Figure 3A:
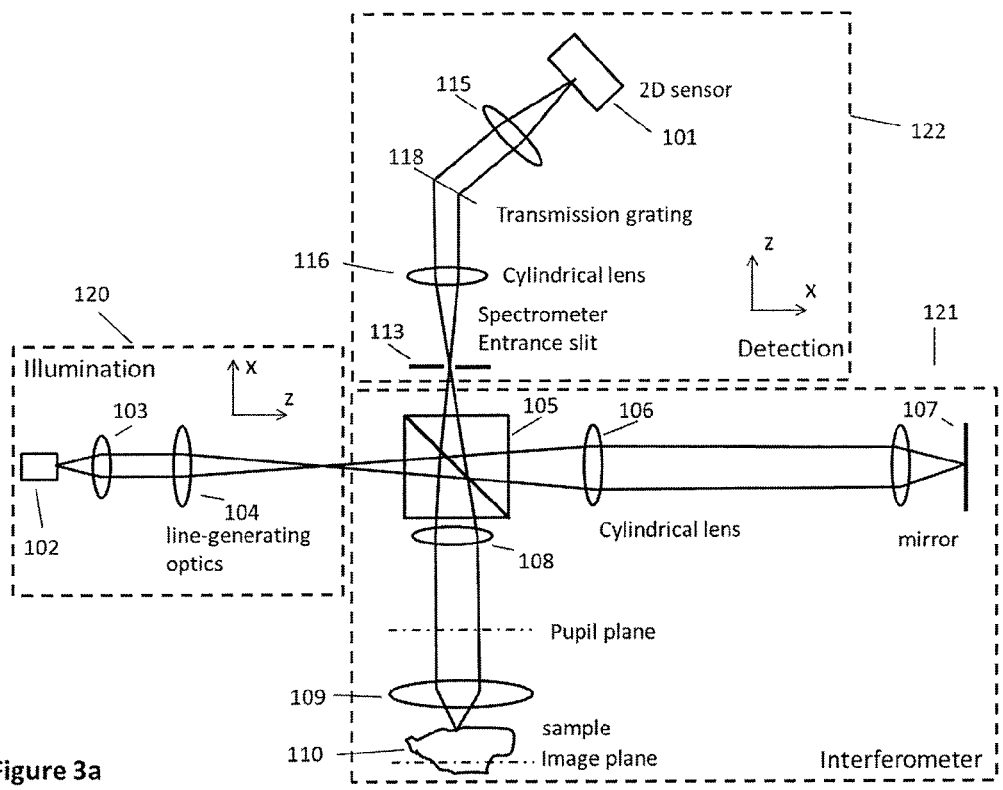
Figure 3B:
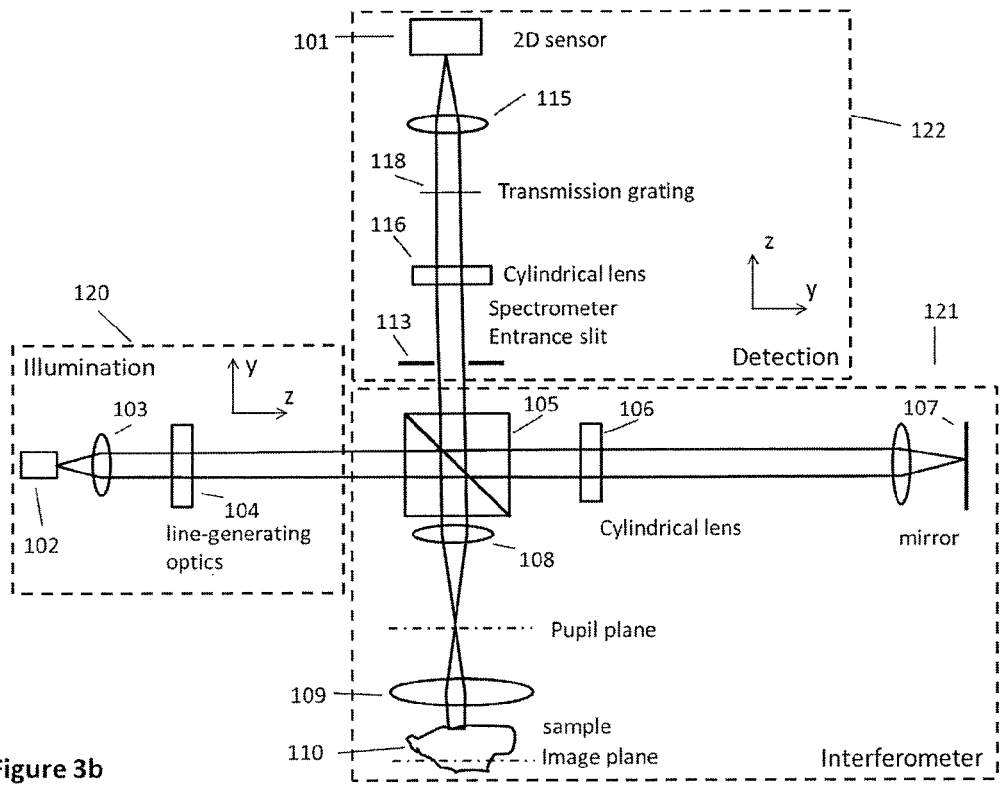

Several alternative embodiments of the invention are possible, and a larger variety of substitutions might be imagined in a more complex arrangement in particular where the conjugate object plane is reimaged more times. For example, in a preferred embodiment of the present invention illustrated in FIG. 3, either of the spherical lenses 114 or 115 in the spectrometer of FIG. 2 might be replaced with a cylindrical lens 116 of the same focal length such that it has no optical power in the y direction. This lens inside the spectrometer replaces and performs the same function as the astigmatic telescope outside the spectrometer entrance slit in the embodiment shown in FIG. 2. FIGS. 3a and 3b show the same views of the corresponding alternative embodiment as are described for FIGS. 2a and 2b. Preferably, both lenses of the spectrometer 116 and 115 might be optimized such that the system acts as a 4F optical system in the spectral dispersing direction (x direction) and as a 2F optical system along the length of the slit such that the sensor is placed at a Fourier plane in this direction. With an asymmetrically curved hologram or other method, these functions may be performed in a single optical element. Note also that many common spectrometer designs, in particular those utilizing off axis reflective optics, inherently introduce significant astigmatism, which could be used to achieve this effect.

The illumination from the reference beam incident upon the confocal limiting aperture of the detector or sensing device may be introduced at an angle relative to the light returning from the sample. This arrangement introduces a phase ramp across the interference data. The phase ramp across the interference data allows for advantages in reconstruction as described by Franke et al. hereby incorporated by reference (Franke et al. High resolution Holoscopy" Proc SPIE 8213 821324 2012).

Figure 4A:
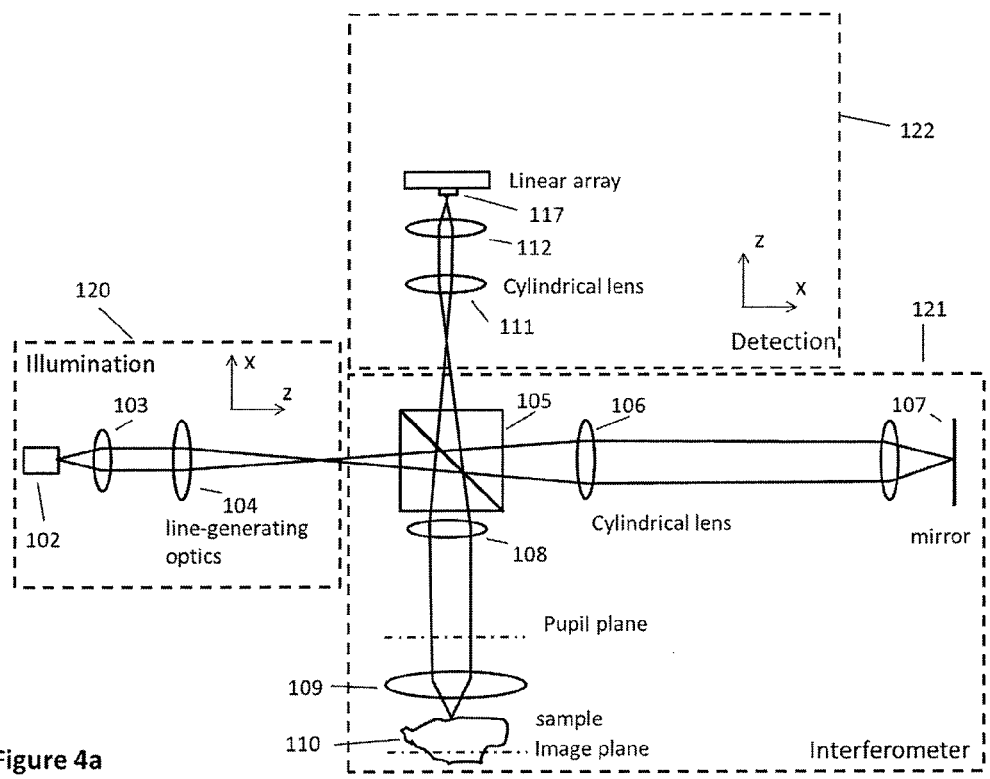
Figure 4B:
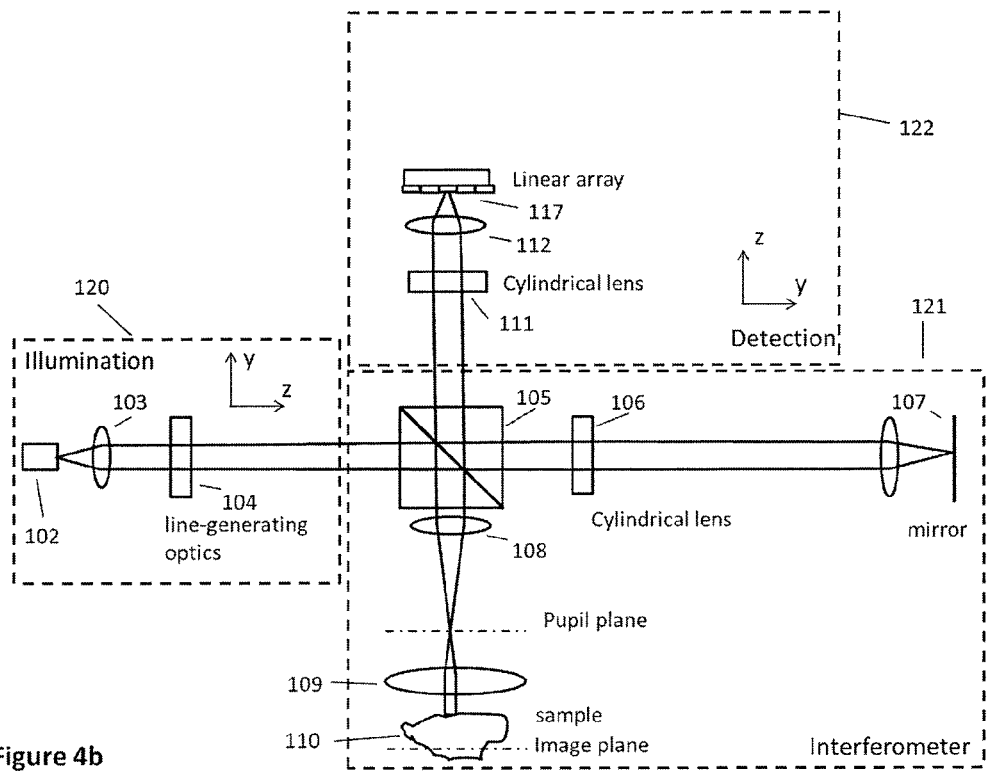

It is also possible to replace the SLD light source with a light source swept in optical frequency, combined with a linear array detector rather than the 2D spectrometer array as is illustrated in FIG. 4. Here a one-dimensional array is placed at the same plane as the spectrometer entrance slit in FIG. 2. The narrow axis of the linear array is in the x-direction and the long axis of the linear array extends in the y-dimension. This arrangement maintains the novel linear confocal gate and holoscopic detection and reconstruction, but transfers some of the design complexity from the spectrometer to the source. In this example the detector is formed simply by the sensor array, provided that the sensor array is sufficiently narrow to provide the desired degree of confocal selection. Alternatively the detector might consist of an entrance slit in combination with a linear detector, in which case the confocal selection is provided without the requirement of a narrow sensor array. Yet another alternative of detection may introduce the astigmatic return optics between the confocal selection device and the linear array. Various detection embodiments consistent with the present invention could be envisioned by those skilled in the art.

Figure 5A:
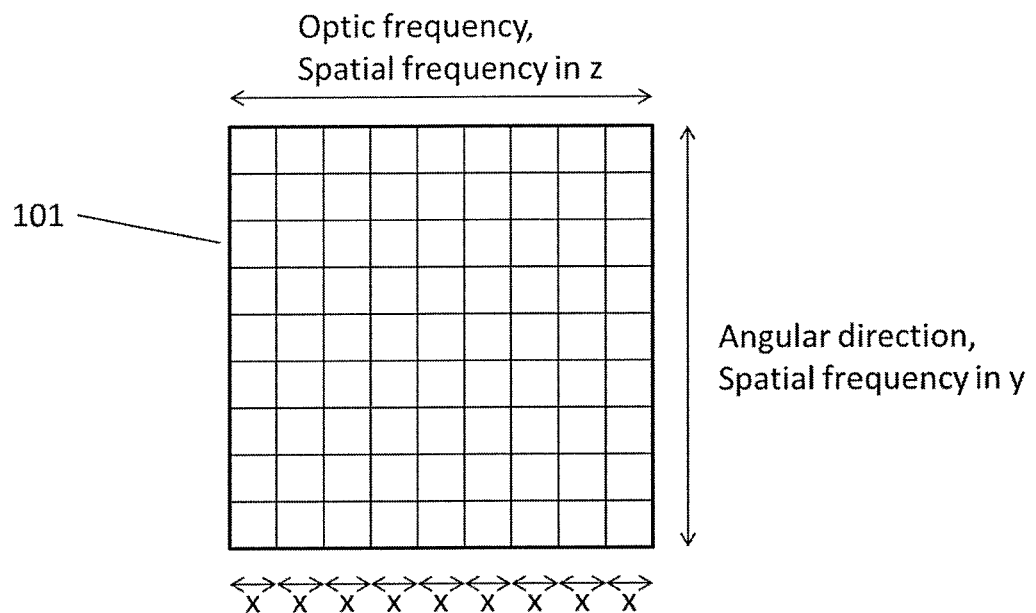
Figure 5B:
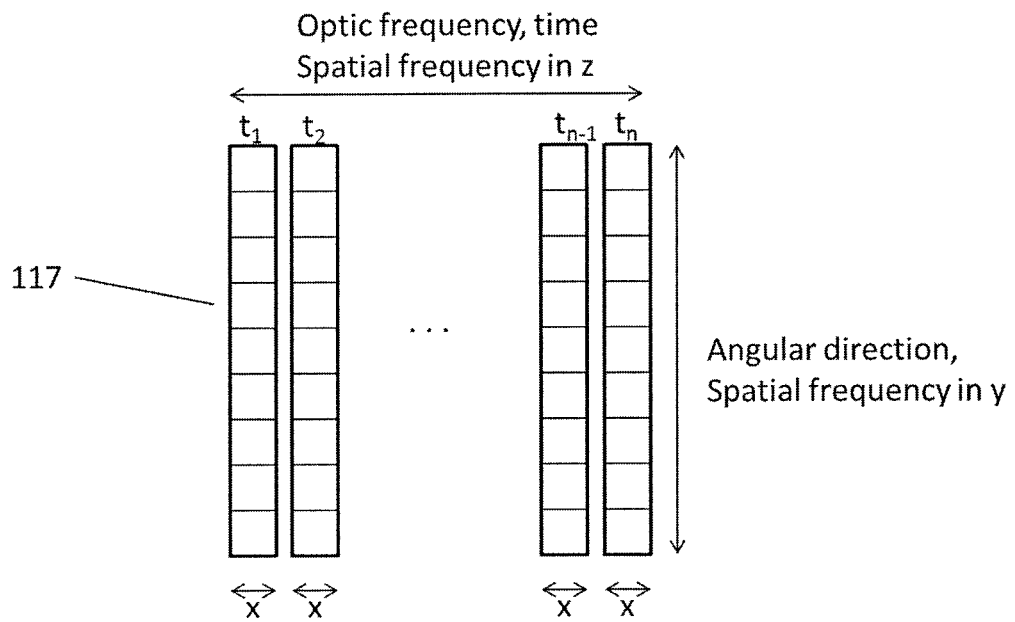

In this embodiment, time can be considered the axis on which optical frequency is encoded at the detector. As illustrated in FIG. 5, with this perspective, the data sets become quite analogous. In FIG. 5a, the 2D sensor array 101 is divided into a y axis encoding spatial frequency in y, and an optical frequency axis, encoding spatial frequency in z. Along each narrow section of the optical frequency axis, the narrow axis of the line illumination is repeated. The narrow x extent of the line (determined by the width of the illuminating line and the spectrometer entrance slit) is convolved with the optical frequency axis. In FIG. 5b, the 1D sensor array 117 is shown repeated at multiple exposures taken at different times corresponding to different optical frequencies produced by the swept source (not shown). The 1D sensor is divided into a y axis encoding spatial frequency in y, whereas the optical frequency axis, encoding spatial frequency in z is encoded in the time of the recording. In this embodiment there is no convolution between the spatial width of the sensor and the optical frequency, however the detector width is managed to maintain the desired 1D confocal gating. One reason to choose the swept source method is to potentially allow greater optical frequency resolution than is easily afforded by the spectrometer approach. The greater optical frequency resolution corresponds to better resolution of the axial spatial frequency, and therefore greater imaging depth after reconstruction.

Further, a scanning mechanism may be added such that multiple line images may be acquired in order to build up greater knowledge of a volume of the sample. The line focus described should be interpreted primarily in terms of its one dimensional confocal gating properties, rather than strictly its geometrical shape. For example, an arc shaped illumination and matching detection selection would provide a similar confocal limitation. The amount of confocal restriction can be modified to some degree to control the amount of out of focus light which reaches the detector. This may be achieved by adjusting width of the line focus (e.g. by adjusting the numerical aperture of the illumination beam if diffraction limited), or by adjusting the width of the detection restriction, or a combination of both.

The invention has application in the imaging of scattering objects, especially for biomedical investigation, in particular the eye and retina. In this case, the sample and nearby optics may be provided by the eye itself. The device may also be used for other biomedical imaging applications such as cardiovascular, dental, cellular, intra-surgical guidance of hollow and solid organs, or for industrial applications such as image based materials inspection.

The invention is particularly beneficial if used to image objects where motion sensitivity is especially critical: e.g. objects that are moving quickly such as living specimens, object where small amounts of motion reduce the value of a measurement such as in the case of corneal curvature.

Although various embodiments that incorporate the teachings of the present invention have been shown and described in detail herein, those skilled in the art can readily devise many other varied embodiments that still incorporate these teachings.

The following references are hereby incorporated by reference:

Patent Literature

DE Patent No. 4309056 Haeusler et al. "Method for determining the distance and intensity of scattering of the scattering points"
U.S. Pat. No. 7,602,501 Ralston et al. "Interferometric Synthetic Aperture Microscopy"
PCT Publication NO. WO 2012/143113 Hillman et al. "Method for Optical Tomography"

Non-Patent Literature

D. Hillmann et al, "Holoscopy—holographic optical coherence tomography" *Optics Letters* 36(13): 2390 2011.
Y. Nakamura, et al, "High-Speed three dimensional human retinal imaging by line field spectral domain optical coherence tomography" *Optics Express* 15(12):7103 2007.
Blazkiewicz et al, "Signal-to-noise ratio study of full-field Fourier-domain optical coherence tomography" *Applied Optics* 44(36):7722 (2005).
Franke et al, "High resolution Holoscopy" Proc SPIE 8213 821324. (2012).
Gaskill, Linear Systems, Fourier Transforms, and Optics John Wiley & Sons, Inc. 1978.
Schnars et al. Digital Holography: Digital Hologram Reporting, Numerical Reconstruction, and Related Techniques Springer 2005

What is claimed is:

1. An interferometric imaging device for imaging a light scattering object comprising:
    a broadband light source arranged to generate a beam of radiation that is swept in frequency;
    a beam divider for separating the beam into reference and sample arms, wherein the sample arm contains the light scattering object to be imaged;
    optics to focus said beam of radiation to a line focus on the light scattering object to be imaged, said line focus having a long axis and a narrow axis;
    collection optics for combining light scattered from the object and light returning from the reference arm, said collection optics also including an astigmatic element for focusing the light along the long axis differently than along the narrow axis;
    a one dimensional sensor array arranged such that the narrow dimension of the line focus is substantially imaged directly to the narrow axis of the sensor array and such that the line focus is defocused along its long axis on the sensor array; and
    a processor for generating an image in response to signals generated by the detector.

2. A device as recited in claim 1, wherein the long axis of the line focus is defocused by at least one Rayleigh length on the sensor array.

3. An interferometric imaging device as recited in claim 2, wherein an angle is introduced between the sample and reference light such that a phase ramp is introduced across the long axis of the detector.

4. An interferometric imaging device as recited in claim 1, wherein the scattering object is a retina of an eye.

5. A device as recited in claim 1, wherein the generation of the image by the processor includes reconstructing the output from the detector to transfer between optical frequency and angular direction to the spatial distribution of scattering in the object, wherein the optical frequency encodes the axial spatial frequency and the angular direction encodes the lateral spatial frequency.

6. A device as recited in claim 5, wherein the generation of the image by the processor includes performing a two-dimensional Fourier transformation of axial spatial frequency and lateral spatial frequency to create a spatial distribution of scattering in the object.

7. An interferometric imaging device for imaging a light scattering object comprising:
    a light source arranged to generate a beam of radiation;
    a beam divider for separating the beam into reference and sample arms, wherein the sample arm contains the light scattering object to be imaged;
    optics to focus said beam of radiation to a line focus on the light scattering object to be imaged, said line focus having a long axis and a narrow axis;
    a detector array;
    collection optics for combining light scattered from the object and light from the reference arm and directing the combined light to the detector; and
    a processor for generating an image in response to signals generated by the detector, wherein digital refocusing is used to obtain high lateral resolution at depths outside of the focused region and wherein the detector array is a one dimensional sensor array arranged such that the narrow dimension of the line focus is substantially imaged directly to the narrow axis of the sensor array and such that the line focus is defocused along its long axis on the sensor array.

8. An interferometric imaging device as recited in claim 7, wherein the collection optics include an astigmatic optic.

9. An interferometric imaging device as recited in claim 7, wherein an angle is introduced between the sample and reference light such that a phase ramp is introduced across the long axis of the detector.

10. An interferometric imaging device as recited in claim 7, wherein the light source is swept in optical frequency.

11. An interferometric imaging device as recited in claim 7, wherein the light source is an SLD.

12. An interferometric imaging device as recited in claim 7, wherein the scattering object is a retina of an eye.

13. An interferometric imaging device as recited in claim 7, wherein the digital refocusing includes reconstructing the output from the detector to transfer between optical frequency and angular direction to the spatial distribution of scattering in the object, wherein the optical frequency encodes the axial spatial frequency and the angular direction encodes the lateral spatial frequency.

14. An interferometric imaging device as recited in claim 7 wherein the digital refocusing is achieved by performing a digital wavefront propagation on the output from the detector to create axial and lateral spatial distributions of scattering in the object.

* * * * *